United States Patent [19]

Kitaoka et al.

[11] Patent Number: 5,591,343
[45] Date of Patent: Jan. 7, 1997

[54] PROCESS FOR EXTRACTION OF CAROTENOIDS FROM BACTERIAL CELLS

[75] Inventors: Motomitsu Kitaoka; Akira Tsubokura; Takashi Kiyota, all of Yokohama, Japan

[73] Assignee: Nippon Oil Co., Ltd., Tokyo, Japan

[21] Appl. No.: 533,390

[22] Filed: Sep. 25, 1995

[30] Foreign Application Priority Data

Sep. 27, 1994 [JP] Japan ..................... 6-231266

[51] Int. Cl.$^6$ .................................................. B01D 11/04
[52] U.S. Cl. .................................. 210/634; 210/511
[58] Field of Search ......................... 210/634, 511; 426/253, 250

[56] References Cited

U.S. PATENT DOCUMENTS

| | | | |
|---|---|---|---|
| 5,120,558 | 6/1992 | Nguyen et al. | 426/425 |
| 5,264,212 | 11/1993 | Mohri et al. | 426/253 X |
| 5,306,637 | 4/1994 | Lin et al. | 435/259 |
| 5,308,759 | 5/1994 | Gierhart | 426/250 X |
| 5,437,997 | 8/1995 | Liao et al. | 435/243 X |

OTHER PUBLICATIONS

WPI Abst. 81–345610, May 5, 1981, Germany.
WPI Abst. 85–084120, Nov. 12, 1996, Japan.
WPI Abst. 94–269632, Jul. 19, 1994, Japan.
WPI Abst. 92–111490, Feb. 25, 1992, Japan.

*Primary Examiner*—Frank Spear
*Attorney, Agent, or Firm*—Seed and Berry LLP

[57] ABSTRACT

A process for extraction of a carotenoid compound from bacterial cells containing the carotenoid compound comprising the step of bringing the bacterial cells into contact with supercritical fluid so as to extract the carotenoid compound from the cells. The process provides carotenoid compounds which can be safely used as feed additives and food additives.

5 Claims, No Drawings

PROCESS FOR EXTRACTION OF CAROTENOIDS FROM BACTERIAL CELLS

CROSS REFERENCE TO RELATED APPLICATIONS

This application claims priority from Japanese Patent Application 6-231,266 filed Sep. 27, 1994, which is incorporated herein by reference in its entirety.

BACKGROUND OF THE INVENTION

1. Field of Invention

The present invention relates to a process for extraction of a carotenoid compound from bacterial cells containing the carotenoid compound.

2. Related Art

Carotenoid compounds are red-yellow series pigments widely distributed in nature, such as in microbial cells, algal cells, and organs and tissues of plants and animals. The carotenoid compounds are used in the field of food additives as coloring agents for foods and beverages, and feed additives for coloring meat or skin of fish such as salmon, trout etc., and for coloring eggs of poultry such as chicken eggs and recently, the use of carotenoid compounds has been expanding. The carotenoid compounds are known to have anti-oxidant action, and are expected to be useful as anti-oxidant agents. In addition, it was recently found that some carotenoid compounds have anti-cancer effect, and therefore are expected to be useful as medicaments.

The carotenoid compounds are classified into those containing an oxygen atom in the molecule and those containing no oxygen atom, and the former are called xanthophyll compounds. Among the xanthophyll compounds, astaxanthin, canthaxanthin, zeaxanthin etc. are industrially produced by chemical synthesis (Pure and Applied Chemistry, 63 (1), 35–44 (1991), and are used as feed additives for coloring.

However, recently it has become difficult to use a chemically synthesized product as food or feed additives due to safety issues, and therefore the development of a process for production of natural carotenoid compounds replacing the chemically synthesized compounds is urgently sought.

For industrial production of carotenoid compounds it is considered that the best process is that comprising culturing bacterial cells to accumulate a carotenoid, recovering the cultured bacterial cells, and extracting the carotenoid compound from the cells, considering the stable supply, high growth rate, high productivity etc.

Japanese Unexamined Patent Publication (Kokai) Nos. 2-138996, 6-165683 and 6-165684 describe methods for extraction of carotenoid compounds from bacterial cells, all of which methods use organic solvents for the extraction. However, since the extracted carotenoid compounds are used as food additives or feed additives, residual solvent may cause problems. Therefore the selection of solvents which can be used for extraction is limited. In addition, xanthophyll compounds which are a group of carotenoid compounds hardly dissolve in solvents which are considered to be safe.

SUMMARY OF THE INVENTION

The present inventors found that the carotenoid compounds can be efficiently extracted with a supercritical fluid without using an organic solvent.

Accordingly the present invention provides a process for extraction of a carotenoid compound comprising the step of bringing microbial cells containing a carotenoid compound into contact with a supercritical fluid.

According to the present invention, the supercritical fluids include various supercritical fluids. A supercritical fluid is a fluid having a distribution constant similar to that of gases, a specific gravity near to that of liquids and a solubilizing power similar to that of liquids.

DETAILED DESCRIPTION

As a supercritical fluid used in the present invention, supercritical carbon dioxide is preferred. The supercritical carbon dioxide is carbon dioxide having a temperature the same as or higher than the critical temperature (31.1° C.) and a pressure the same as or higher than the critical pressure (75.2 $kgf/cm^2$).

According to the present invention, extraction is carried out in a pressure-resistant container by bringing a supercritical fluid alone or in combination with an entrainer into contact with bacterial cells to be extracted, although other methods can be used.

In the case where an entrainer is used, the amount of the entrainer is usually at most 100% by weight relative to the supercritical fluid, though the amount is not limited thereto. As the entrainer, water, methanol, ethanol, isopropylalcohol (IPA), acetone, ethyl acetate, hexane etc. are preferably used considering the safety of the residual solvent, though other solvents may be used as well.

Any extraction temperature the same as or higher than the critical temperature of the supercritical fluid used can be used. If supercritical carbon dioxide is used, the extraction temperature is same as or higher than the critical temperature of carbon dioxide, i.e., 31.1° C., and usually up to 100° C., more preferably up to 60° C., and even more preferably up to 45° C.

Any extraction pressure the same as or higher than the critical pressure of a supercritical fluid used can be used. If supercritical carbon dioxide is used, the extraction pressure is the same as or higher than the critical pressure of carbon dioxide, i.e, 75.2 $kgf/cm^2$, and usually up to 500 $kgf/cm^2$, and preferably 250 $kgf/mm^2$.

The extraction time is not critical, but preferably at least one second, preferably one minute, and more preferably at least 10 minutes, and up to 100 hours, and preferably up to 10 hours.

The amount of supercritical fluid used is not critical, and usually at least 1 mg and preferably at least 10 mg, and up to 10 g and preferably up to 5 g, per 1 mg of bacterial cells.

The materials to be subjected to the present extraction may be any bacterial cells containing a carotenoid compound. Examples of such bacterial cells are those obtained by culturing a bacterium having an ability to produce at least one carotenoid compound selected from the group consisting of astaxanthin, adonixanthin, β-carotene, echinenone, canthaxanthin and zeaxanthin, such as the E-396 strain (FERM BP-4283) in a medium containing a carbon source, nitrogen source, inorganic salts and if necessary other required substance (for example, vitamins, amino acids, nucleotides etc.), and centrifuging or filtering the culture or by other conventional methods. Alternatively, the present cells containing a carotenoid can be obtained by culturing a bacterium belonging to the genus Corynebacterium having an ability to produce canthaxanthin, such as Corynebacterium SQH348 (FERM BP-4284) in a medium containing carbon source, nitrogen source, inorganic salts and if necessary other required substances (for example, vitamins, amino acids, nucleotides et al.), and recovering the cells by centrifugation or filtration. Again, the bacterial cells of the present invention are not limited to those exemplified above.

Bacterial cells to be subjected to extraction may be wet cells, dried cells, or cells suspended in a solvent. The carotenoid compounds to be extracted are any carotenoid compounds. The present invention is especially useful for extraction of the xanthophyll compounds which are not usually extracted by any conventional process. The carotenoids extracted according to the present invention are, for example, astaxanthin, canthaxanthin, zeaxanthin, adonixanthin, echinenone, cryptoxanthin, adonirubin, asteroidenon, rhodoxanthin, 3-hydroxyechinenon, astaxanthin ester, β-carotene, α-carotene, γ-carotene, lycopene, capsanthin, β-zeacarotene, torulene, flanoxanthin, α-doracarotene, fucoxanthin, phoenicoxanthin etc.

According to the present invention, bacterial cells containing at least one of the above-mentioned carotenoid compounds can be used. Especially, bacterial cells containing at least one of astaxanthin, canthaxanthin, zeaxanthin, adonixanthin, echinenone, cryptoxanthin, adonirubin and asteroidenone are preferably used.

EXAMPLES

Next, the present invention is further explained by the following examples, although it is not limited thereto.

Preparative Example 1

An astaxanthin and adonixanthin-producing bacterium E-396 (FERM BP-4283) was cultured in 30 L of a medium containing 20 g/L yeast extract, 30 g/L sucrose, 1.5 g/L $KH_2PO_4$, 1.5 g/L $Na_2HPO_4$, 0.5 g/L $MgSO_4·7H_2O$, 0.01 g/L $FeSO_4·7H_2O$, 0.01 g/L $CaCl_2$ adjusted to pH 7.0 with $Na_2CO_3$ for 5 days, and the cultured cells were centrifuged to obtain 900 g of wet cells. The wet cells contained 1.0 mg/g of carotenoid compounds. 300 g of the wet cells thus obtained was lyophilized to obtain 57 g of lyophilized cells.

Examples 1 to 20

50 mg of the dried cells of E-396 (FERM BP-4283) was added to a HPLC column having a capacity of 2.5 ml, and the column was connected to a supercritical chromatography apparatus (Nippon Denshi K.K.). Extraction was carried out by passing supercritical carbon dioxide through the column at a flow rate of 92 mg/min. If an entrainer was used, extraction was carried out by flowing the supercritical carbon dioxide at a flow rate of 92 mg/min. and the entrainer at a flow rate of 20 μL/min.

The extraction temperature, extraction pressure and extrainer conditions were varied as shown in Table 1, and the results shown in Table 1 were obtained. An extraction ratio is the ratio of the amount of extracted carotenoid to the amount of carotenoid contained in the cells prior to the extraction.

TABLE 1

| Example | Extraction temperature °C. | Extraction pressure kgf/cm² | Extraction time min | Entrainer | Extraction ratio % |
|---|---|---|---|---|---|
| 1 | 35 | 200 | 30 | No | 42 |
| 2 | 35 | 200 | 60 | No | 63 |
| 3 | 35 | 200 | 120 | No | 75 |
| 4 | 35 | 200 | 240 | No | 92 |
| 5 | 40 | 200 | 60 | No | 55 |
| 6 | 50 | 200 | 120 | No | 38 |
| 7 | 35 | 250 | 60 | No | 64 |
| 8 | 35 | 150 | 60 | No | 59 |
| 9 | 35 | 100 | 60 | No | 41 |
| 10 | 35 | 100 | 60 | Methanol | 70 |
| 11 | 35 | 150 | 60 | Methanol | 75 |
| 12 | 35 | 200 | 60 | Methanol | 79 |
| 13 | 35 | 100 | 120 | Methanol | 93 |
| 14 | 35 | 100 | 60 | IPA | 95 |
| 15 | 35 | 150 | 60 | IPA | 93 |
| 16 | 35 | 200 | 60 | IPA | 93 |
| 17 | 35 | 100 | 120 | IPA | 99 |
| 18 | 35 | 100 | 60 | Acetone | 64 |
| 19 | 35 | 150 | 60 | Acetone | 67 |
| 20 | 35 | 200 | 60 | Acetone | 66 |

Examples 21 to 40

100 mg of the wet cells of E-396 (FERM BP-4283) was spread on a rectangular mesh, and the mesh was added to a HPLC column having a capacity of 2.5 mL. The column was connected to a supercritical chromatography apparatus, and extraction was carried out under the same condition as described above.

The extraction temperature, extraction pressure and entrainer conditions were varied as shown in Table 2, and the results are shown in Table 2. The extraction ratio is the ratio of the amount of extracted carotenoid to the amount of carotenoid contained in the cells prior to the extraction.

TABLE 2

| Example | Extraction temperature °C. | Extraction pressure kgf/cm² | Extraction time min | Entrainer | Extraction ratio % |
|---|---|---|---|---|---|
| 21 | 35 | 200 | 30 | No | 42 |
| 22 | 35 | 200 | 60 | No | 63 |
| 23 | 35 | 200 | 120 | No | 75 |
| 24 | 35 | 200 | 240 | No | 92 |
| 25 | 40 | 200 | 60 | No | 55 |
| 26 | 50 | 200 | 120 | No | 38 |
| 27 | 35 | 250 | 60 | No | 64 |
| 28 | 35 | 150 | 60 | No | 59 |
| 29 | 35 | 100 | 60 | No | 41 |
| 30 | 35 | 100 | 60 | Methanol | 70 |
| 31 | 35 | 150 | 60 | Methanol | 75 |
| 32 | 35 | 200 | 60 | Methanol | 79 |
| 33 | 35 | 100 | 120 | Methanol | 93 |
| 34 | 35 | 100 | 60 | IPA | 95 |
| 35 | 35 | 150 | 60 | IPA | 93 |
| 36 | 35 | 200 | 60 | IPA | 93 |
| 37 | 35 | 100 | 120 | IPA | 99 |
| 38 | 35 | 100 | 60 | Acetone | 64 |
| 39 | 35 | 150 | 60 | Acetone | 67 |
| 40 | 35 | 200 | 60 | Acetone | 66 |

Example 41

10 g of the dried cells of E-396 (FERM BP-4283) was put into a 100 mL-high pressure container, and supercritical carbon dioxide at a temperature of 35° C. and a pressure of 150 kgf/cm² was passed through the container at a flow rate of 10 g/min. for 2 hours to extract carotenoid compounds. As a result, an extraction ratio was 75%.

Example 42

10 g of the dried cells of E-396 (FERM BP-4283) was mixed with 20 ml of isopropanol and the mixture was added to a 100 ml high pressure container. Supercritical carbon dioxide at a temperature of 35° C. and a pressure of 150 kgf/cm² was passed through the container at a flow rate of 10 g/min. for 2 hours to extract carotenoid compounds. As a result, the extraction ratio of the carotenoid compound was 97%.

Example 43

20 g of the wet cells of E-396 (FERM BP-4283) was added to a 100 ml high pressure container, and supercritical carbon dioxide at a temperature of 35° C. and a pressure of 150 kgf/cm² was passed through the container at a flow rate of 10 g/min. for 2 hours to extract carotenoid compounds. As a result, the extraction ratio of the carotenoid compound was 64%.

Example 44

20 g of the wet cells of E-396 (FERM BP-4283) was mixed with 20 mL of isopropanol, and the mixture was added to a 100 mL high pressure container. Supercritical carbon dioxide at a temperature of 35° C. and a pressure of 150 kgf/cm² was passed through the container at a flow rate of 10 g/min. for 2 hours to extract carotenoid compounds. As a result, the extraction ratio of the carotenoid compound was 95%.

Preparative Example 2

A canthaxanthin-producing strain, Corynebacterium sp. SQH348 (FERM BP-4284), was cultured in 3 L of a medium containing 30 g/L yeast extract, 10 g/L glucose, 5 ml/L soy bean oil, 2.5 g/L $NH_4NO_3$, 1.5 g/L $KH_2PO_4$, 1.5 g/L $Na_2HPO_4$, 0.5 g/L $MgSO_4 \cdot 7H_2O$, 0.01 g/L $FeSO_4 \cdot 7H_2O$ and 0.01 g/L $CaCl_2$, adjusted to pH 8.0 with $Na_2CO_3$ for 7 days, and the culture was centrifuged to obtain 75 g of the wet cells. The wet cells contained 0.61 mg/g carotenoid compounds. 40 g of the wet cells was lyophilized to obtain 8.6 g of lyophilized cells.

Examples 45 to 49

50 mg of the dried cells of Corynebacterium sp. SQH348 (FERM BP-4284) was filled in a HPLC column having a capacity of 2.5 mL, and the column was connected to a supercritical chromatography apparatus (Nippon Denshi K.K.). Extraction was carried out by passing supercritical carbon dioxide through the column at a flow rate of 92 mg/min. If an entrainer was used, the supercritical carbon dioxide was flowed at a flow rate of 92 mg/min. and the entrainer was flowed at a flow rate of 20 µL/min. The results are shown in Table 3.

Examples 50 to 54

100 mg of the wet cells of Corynebacterium sp. SQH348 (FERM BP-4284) was spread on a rectangular mesh, which was then added to a HPLC column having a capacity of 2.5 mL. The column was joined to a supercritical chromatography apparatus. Extraction was carried out under the same conditions as described in Examples 45 to 49. The results are shown in Table 3.

TABLE 3

| Example | Extraction temperature °C. | Extraction pressure kgf/cm² | Extraction time min | Entrainer | Extraction ratio % |
|---|---|---|---|---|---|
| 45 | 35 | 200 | 120 | No | 78 |
| 46 | 35 | 100 | 120 | No | 66 |
| 47 | 35 | 100 | 60 | Methanol | 74 |
| 48 | 35 | 100 | 60 | IPA | 94 |
| 49 | 35 | 100 | 60 | Acetone | 68 |
| 50 | 35 | 200 | 120 | No | 72 |
| 51 | 35 | 100 | 120 | No | 59 |
| 52 | 35 | 100 | 60 | Methanol | 71 |
| 53 | 35 | 100 | 60 | IPA | 90 |
| 54 | 35 | 100 | 60 | Acetone | 65 |

According to the present invention, carotenoid compounds, especially xanthophyll compounds, can be efficiently extracted from bacterial cells. Carotenoid compounds produced by the present invention can be safely used as feed additives and food additives.

We claim:

1. A process for extraction of a carotenoid compound from bacterial cells containing the carotenoid compound comprising the step of bringing the bacterial cells into contact with a supercritical fluid so as to extract the carotenoid compound from the bacterial cells, wherein an entrainer selected from the group consisting of methanol and isopropanol is used in combination with the supercritical fluid.

2. A process according to claim 1, wherein the carotenoid compound is a xanthophyll compound.

3. A process according to claim 1, wherein the supercritical fluid is supercritical carbon dioxide.

4. A process according to claim 1, wherein an amount of the supercritical fluid used is between 1 mg and 10 g per 1 mg bacterial cells.

5. A process according to claim 1, wherein the entrainer is used in an amount of up to 100% by weight relating to an amount of supercritical fluid.

* * * * *